US012630490B2

(12) United States Patent
Trejo OReilly et al.

(10) Patent No.: US 12,630,490 B2
(45) Date of Patent: May 19, 2026

(54) PROCESS FOR PREPARATION OF A SUGAR ALCOHOL

(71) Applicants: DDP SPECIALTY ELECTRONIC MATERIALS US 8, LLC, Wilmington, DE (US); DUPONT SAFETY & CONSTRUCTION, INC., Wilmington, DE (US)

(72) Inventors: Jose Antonio Trejo OReilly, Lansdale, PA (US); Sourav Kumar Sengupta, Wilmington, DE (US); Jonathan M. Bingaman, Birdsboro, PA (US)

(73) Assignees: DDP SPECIALTY ELECTRONIC MATERIALS US 8, LLC, Wilmington, DE (US); DUPONT SAFETY & CONSTRUCTION, INC., Wilmington, DE (US)

( * ) Notice: Subject to any disclaimer, the term of this patent is extended or adjusted under 35 U.S.C. 154(b) by 447 days.

(21) Appl. No.: 18/006,970

(22) PCT Filed: Jul. 21, 2021

(86) PCT No.: PCT/US2021/042493
§ 371 (c)(1),
(2) Date: Jan. 26, 2023

(87) PCT Pub. No.: WO2022/026262
PCT Pub. Date: Feb. 3, 2022

(65) Prior Publication Data
US 2023/0278941 A1 Sep. 7, 2023

Related U.S. Application Data

(60) Provisional application No. 63/057,918, filed on Jul. 29, 2020.

(51) Int. Cl.
*C07C 29/141* (2006.01)
*B01D 15/36* (2006.01)

(52) U.S. Cl.
CPC .......... *C07C 29/141* (2013.01); *B01D 15/361* (2013.01); *C07C 2523/46* (2013.01)

(58) Field of Classification Search
CPC ... C07C 29/141; C07C 2523/46; C07C 31/26; B01D 15/361
See application file for complete search history.

(56) References Cited

U.S. PATENT DOCUMENTS 6,291,725 B1 * 9/2001 Chopade ................. C07C 29/00
568/864
2010/0099933 A1 * 4/2010 Yao ......................... C08B 15/00
585/310

FOREIGN PATENT DOCUMENTS

EP         2402086 A1 * 1/2012 .............. B01J 35/40
JP      2014097951 A * 5/2014 ........... C07C 29/141

* cited by examiner

*Primary Examiner* — Yate' K Cutliff

(57) ABSTRACT

A method for reduction of sugars. The first step is providing a solution of a sugar comprising from five to twenty carbon atoms. The second step is contacting said solution with hydrogen gas and a catalyst. The catalyst is an ion exchange resin comprising Ru.

11 Claims, No Drawings

PROCESS FOR PREPARATION OF A SUGAR ALCOHOL

BACKGROUND

This invention relates generally to a method for reduction of sugars and preparation of a sugar alcohol from a sugar.

Reduction of glucose to sorbitol by hydrogenation using several transition metals as heterogeneous catalysts is known. For example, V. N. Sapunov et al., *J. Phys. Chem. A,* 2013, 117, 4073-4083, discloses reduction of glucose to sorbitol with ruthenium embedded in a hyper-crosslinked polystyrene matrix. However, this reference reports low conversions of glucose and also uses special procedures to embed ruthenium in the hyper-crosslinked polymer matrix. Alternative heterogeneous reduction systems for sugars would be useful.

STATEMENT OF INVENTION

The present invention is directed to a method for reduction of sugars. The method comprises steps of:
  a) providing a solution of a sugar comprising from five to twenty carbon atoms; and
  b) contacting said solution with hydrogen gas and a catalyst;
wherein said catalyst comprises an ion exchange resin comprising Ru.

DETAILED DESCRIPTION

All percentages are weight percentages (wt %), and all temperatures are in ° C., unless otherwise indicated. Averages are arithmetic averages unless indicated otherwise. All operations are performed at room temperature (from 18 to 25° C.) unless specified otherwise. Percentages of monomers are based on the weight of dry polymer, i.e., dry ion exchange resin beads, and the same percentages apply to the monomer mixture used to produce the beads. The terms "(meth)acrylate" and "(meth)acrylic" mean acrylate or methacrylate, and acrylic or methacrylic, respectively. References to transition metals, e.g., ruthenium, indicate the zero-valent metal. Particle size is determined using a dynamic imaging particle analyzer, e.g., a FlowCam™ Macro analyzer and the average stated herein as the harmonic mean size (HMS).

Preferably, the harmonic mean size of the ion exchange resin is at least 200 microns, preferably at least 300 microns, preferably at least 400 microns; preferably no greater than 1100 microns, preferably no greater than 1000 microns, preferably no greater than 900 microns, preferably no greater than 800 microns, preferably no greater than 700 microns.

Preferably, the particle size distribution has a Uniformity Coefficient of at least 1.01, not greater than 1.2 for Uniform Particle Size (UPS) resins and not greater than 1.6 for Normal particle size distribution resins. UPS resins are those produced by jetting monomer droplets into an aqueous phase synthesis and Normal particle size distribution resins are manufactured in stirred reactors.

Useful ion exchange resins include strong acid cation exchange resins, weak acid cation exchange resins, strong base anion exchange resins and weak base anion exchange resins. Preferably, the ion exchange resin is a cation exchange resin, preferably a strong acid cation exchange resin, i.e., one having sulfonic acid groups. Preferred ion exchange resins may be acrylic (>70 wt % polymerized units of acrylic monomers, preferably >85 wt %) or styrenic (>70 wt % polymerized units of styrene or a substituted styrene, preferably >85 wt %). In a preferred embodiment of the invention, the ion exchange resin is a gel resin (surface area <5 m²/g dry resin as measured by the BET technique), preferably a gel resin comprising no more than 10 wt % polymerized units of crosslinker, preferably no more than 8 wt %, preferably no more than 7 wt %, preferably no more than 6 wt %; preferably at least 1 wt %, preferably at least 2 wt %, preferably at least 2.5 wt %, preferably at least 3 wt %. In another preferred embodiment, the ion exchange resin is a macroreticular resin. Macroreticular resins preferably have a surface area from 10 to 100 m²/g, preferably from 20 to 50 m²/g. Preferably, macroreticular resins have a total porosity of 0.1 to 0.9, preferably 0.2 to 0.7, preferably 0.25 to 0.5 cm³/g, with an average pore diameter of 50 to 2500 Angstroms and preferably from 150 to 1000 Angstroms. Porosities are defined according to IUPAC (International Union of Pure and Applied Chemistry) nomenclature as follows: Microporosity=pores less than 20 Angstrom units
  Mesoporosity=pores between 2- and 500 Angstrom units
  Macroporosity=pores greater than 500 Angstrom units.
Preferably, macroreticular resins comprise at least 8 wt % polymerized units of crosslinker, preferably at least 10 wt %, preferably at least 12 wt %; preferably no more than 20 wt %, preferably no more than 19 wt %, preferably no more than 17 wt %.

Preferred crosslinkers include divinylbenzene, trivinylcyclohexane, TMPTMA (trimethylol propane trimethacrylate) and DEGDVE (diethylene glycol divinyl ether); preferably divinylbenzene. Preferably, the ion exchange resin comprises from 80 to 99 wt % polymerized units of monofunctional monomer. Preferred monofunctional monomers include vinyl aromatic monomers (e.g., styrene, methylstyrene, ethylstyrene, α-methylstyrene; preferably styrene) and acrylic monomers (alkyl (meth)acrylates, (meth)acrylic acid). Preferably, a styrenic ion exchange resin has acidic sites in an amount from 0.9 to 2.5 eq./liter of resin; preferably at least 1.3 eq./liter, preferably no more than 1.8 eq./liter. Preferably, an acrylic ion exchange resin has acidic sites in an amount from 3.0 to 5.5 eq./liter of resin; preferably at least 3.5 eq./liter, preferably no more than 5.0 eq./liter. Preferably, a styrenic ion exchange resin has acidic sites in an amount from 2.5 to 5.3 eq./kg dry resin; preferably at least 4.2 eq./kg dry resin, preferably no more than 5.0 eq./kg dry resin.

Preferably, total loading of Ru on the ion exchange resin is from 0.5 to 200 g/liter of resin; preferably at least 1 g/liter, preferably at least 2 g/liter, preferably at least 5 g/liter, preferably at least 10 g/liter, preferably at least 20 g/liter; preferably no more than 100 g/liter of resin, preferably no more than 80 g/liter, preferably no more than 70 g/liter, preferably no more than 60 g/liter. In a preferred embodiment of the invention, the catalyst comprises Ru and at least one of Mo, W, V, Mn, Ni, Cu, Zn, Cr, Ge, Sn, Ti, Au, and Zr; preferably at least one of Mo, W, Ni, Cu, and Sn. Preferably, the total loading of metal on the ion exchange resin is from 0.5 to 200 g/liter of resin; preferably at least 1 g/liter, preferably at least 2 g/liter, preferably at least 5 g/liter, preferably at least 10 g/liter, preferably at least 20 g/liter; preferably no more than 100 g/liter of resin, preferably no more than 80 g/liter, preferably no more than 70 g/liter, preferably no more than 60 g/liter.

The sugar is provided as a solution, preferably an aqueous solution, i.e., a solution in which the primary solvent is water, preferably at least 50 vol % water, preferably at least 75%, preferably at least 85%. Preferably, the concentration of sugar is from 10 to 65 wt %, preferably from 30 to 40 wt % Preferably, the sugar comprises from five to twenty carbon atoms; preferably at least six carbon atoms; preferably no more than 18 carbon atoms, preferably no more than 17, preferably no more than 16, preferably no more than 15, preferably no more than 12. Preferred sugars include ribose, arabinose, xylose, lyxose, glucose, fructose, mannose, galactose, sedoheptulose, mannoheptulose, and sucrose; preferably glucose, fructose, and mannose; preferably glucose. Preferably, the sugar is a monosaccharide or polysaccharide; preferably a monosaccharide or disaccharide; preferably a monosaccharide.

Preferably, the catalyst is prepared by contacting the ion exchange resin with an aqueous solution of the metal salt(s), followed by reduction of the metal ion(s) with a reducing agent. Preferred reducing agents include sodium borohydride, hydrogen, hydrazine, formaldehyde, and lithium aluminum hydride; preferably sodium borohydride. The initial metal salt may be reduced to a lower positive valence state than the original metal ion in solution or reduced completely to the zero-valent metal. Preferably, the catalyst comprises zero-valent metal. Preferably, the reducing agent contains sodium or potassium cations. Preferably the acid groups in the resin remain as metal salt(s) with Na, K, Ca, Mg, Ba, Fe or Al cations; preferably Na, K, Ca or Mg cations. The acid groups on a resin could also be in the acid form as —SO$_3$H if the resin loaded with a metal salt is reduced with hydrogen. Preferably the acid groups in the resin remain as acid (H+) when metal is reduced with hydrogen.

Preferably, hydrogenation of the sugar solution is carried out at a temperature from 25 to 180° C.; preferably at least 40° C., preferably at least 60° C., preferably at least 80° C., preferably at least 100° C., preferably at least 115° C., preferably at least 125° C.; preferably no greater than 170° C., preferably no greater than 160° C., preferably no greater than 150° C. Preferably, the hydrogenation of the sugar solution is carried out at a hydrogen pressure from 40 to 600 psi (275 kPa to 4.2 MPa); preferably at least 60 psi (410 kPa), preferably at least 100 psi (690 kPa), preferably at least 150 psi (1.0 MPa), preferably at least 200 psi (1.4 MPa); preferably no greater than 500 psi (3.5 MPa), preferably no greater than 400 psi (2.8 MPa). Preferred reaction times may vary from 0.25 to 15 hours, preferably 0.5 to 5 hours. Preferred pressures, times and temperatures as described above are not considered to be critical parameters (especially upper limits on time and pressure) and the combination of these parameters may be adjusted by one skilled in the art to achieve the desired conversion and reaction time efficiently. The hydrogenation may be done in batch mode using a stirred tank reactor, in continuous stirred tank reactors in series, in continuous slurry bubble column reactors, and in continuous multitubular reactors. Preferably, a continuous method for making sorbitol utilizes a mixing vessel and a fixed bed catalytic reactor containing a solid acid catalyst. An aqueous solution of glucose is introduced into the mixing vessel. Hydrogen is sparged in the mixing vessel. The glucose solution is pumped in to the catalytic reactor along with hydrogen. The desired product sorbitol generated in the fixed bed reactor in the aqueous solution exits the process, with part of the exit stream recycled back into the process.

Analysis for Sorbitol and Quantification methods used:

Method I: Chromatography

Quantitative Ion Exclusion Chromatography method used the following conditions: Column: Aminex HPX-87H Ion Exclusion Column. Column Temperature: 80° C.

Detector: Agilent 1260 RID (G7162A). RID Temperature: 50° C.

Flow rate: 0.4 mL/min. Injection volume: 2 μL

Calibration of areas and concentrations were done using standards from Sigma Aldrich for Sorbitol, Mannitol, Glucose, Fructose and other peaks found as side products were reported as unknows.

Calculations Using HPLC Data were Done by the Following:

Conversion (%)=100−[Glucose(time zero)/Glucose (time x)]*100

Selectivity (%)=Sorbitol(peak)/(Sum of all peaks−Glucose peak)*100

Yield (%)=Conversion*Selectivity

Method II: NMR

Quantitative 1D $^1$H NMR data was collected on an Agilent DD2 or Bruker NEO Spectrometer operating at 500 MHz maintained by operators skilled in the art. The spectra were acquired with 8 transients, recycle delay of 30 sec, 90° pulse width, acquisition time of 3.17 sec, 25.8 kHz spectral window and 82 k points. Data processing was performed in Bruker Topspin software. Raw data was zero-filled to 131 k data points and processed with 0.3 Hz exponential multiplication. Resulting NMR spectrum was phased, and baseline corrected. Chemical Shift was referenced to D$_2$O=4.65 ppm. Integrals for analytes were corrected for slope and bias. The conversion was calculated from the mol ratios of glucose and sorbitol obtained from the processed NMR spectrum as follows:

% Yield=((mols sorbitol)/(mols sorbitol+mols glucose))*100

Mols of sorbitol was determined from the resonances which are resolved from glucose. The mol number of protons in this area was found to be 3 based on comparison with authentic reference spectrum with total integral area normalized to 8.

Mots sorbitol=∫(δ3.54 ppm to 3.44 ppm)/3;complex

Mols of glucose was measured as the sum of the anomeric protons corresponding to αβ-glucose.

Mots glucose=∫(δ5.12 ppm to 5.04 ppm)+∫(δ4.52 ppm to 4.47 ppm);α/βanomeric protons Catalyst Synthesis and Metal Impregnation—Reduction Preparation of Metal-Supported Ion-Exchange Resin Catalysts Commercial ion exchange resins (e.g. AMBERLYST™ 15, 131, 35, and 46 resins) and aqueous Ru and Ni salt (RuCl$_3$·xH$_2$O, NiCl$_2$·6H$_2$O, and NiSO$_4$·xH$_2$O) solutions were used to prepare metal-supported ion-exchange resin catalysts. The catalysts used for the metal impregnation were resins in the initial ionic salt forms: H, Na or Ca. Examples of this ionic forms of commercially available resins are: AmberLite CR99 310 Ca, AmberLite FPC16UPS Na and AmberLite FPC88 UPS H. The metal impregnation used two different methods: a) Incipient Wetness or b) Ion Exchange in Water and are described in the following paragraphs. The next general process once the metal has impregnated the resin is the reduction to zero valence state following one of the following procedures: a) Hydrogenation or b) NaBH$_4$ solution.

Incipient Wetness Method:

The amount of metal to load into the resin (based on the desired metal loading) and water needed to swell the resin were calculated. The solution of metal salt was prepared based on the above calculation. The resin was dried overnight in a vacuum oven at 100° C. The dried resin was placed in a large beaker and the aqueous solution containing the metal salt (20% water used to ensure complete wetting of the resin) dropwise. The wetted beads comprising the metal salt was left for ~30 minutes for full adsorption. The beaker was then placed in an ice bath and 12% $NaBH_4$ in 14M NaOH solution was slowly added to the resin, using a pipette. (Caution: This reaction can be very violent depending on the chosen metal loading; high metal loadings will result in a lot of bubbling/foaming/heating). Once the violent bubbling stopped, the beaker was removed from the ice bath and allowed to reduce overnight. The reduced metal-supported ion-exchange resin catalyst was then transferred on to a Buchner funnel and rinsed with water until the wash water resulted in a neutral pH (pH ~6 or 7). The catalyst, so prepared, was ready for use for activity testing or catalyst characterization. Optionally, the catalyst can also be dried in a vacuum oven (dried resin mass was more consistent than wetted). All catalysts contained 2.5 g-Ru/Liter resin.

Ion Exchange in Water Metal Loading:

The amount of metal to load into the resin based on the %-w loading objective for the desired metal loading for each resin is calculated. The solution of metal salt was prepared in water adding some hydrochloric acid and mixing all with the resin. This mixture is agitated for 24 h to equilibrate and metal to be exchanged into the sulfonic sites. At the end of the time in agitation the resin is Buchner dried and could be then subject for reduction process for the metal. Could be dried or wet version of the resin for the reduction with sodium borohydride ($NaBH_4$/NaOH aqueous solution) or Hydrogen in columns or reactors.

EXAMPLES

Selected Examples for the Synthesis Process Explained and Results for all the Catalysts.

Example: AmberLyst™ 15 WET 5% Ru Impregnated and Sodium Borohydride Reduction Step 10 mL AmberLyst™ 15 WET charged into a reactor. 0.225 g $RuCl_3$, 0.2 g HCl and 50 mL HPLC grade water was mix into an agitated vessel. Agitation at 200 rpm at room temperature done overnight. The content of the reactor are filtered and the metal impregnated resin isolated. The resin was then dried at 70° C. overnight in a vac oven with Nitrogen sweep. Yield was 9 mL catalyst wet 5%-w Ru. Reduction of the metal to zero valent was achieved using sodium borohydride procedure exemplified as follows: 50 mL Sodium borohydride solution was added to the wet catalyst in a beaker. After 3 hours the reaction is finished, and resin is washed with excess HPLC water grade, filtered and dried at 90° C. overnight in vacuum oven under nitrogen sweep condition.

Example: AmberLyst™ 15 WET 1% Ru Impregnated and Sodium Borohydride Reduction Step 10 mL AmberLyst™ 15 WET charged into a reactor. 0.045 g $RuCl_3$, 0.2 g HCl and 50 mL HPLC grade water was mix into an agitated vessel. Agitation at 200 rpm at room temperature done overnight. The content of the reactor are filtered and the metal impregnated resin isolated. The resin was then dried at 70° C. overnight in a vac oven with Nitrogen sweep. Yield was 9 mL catalyst wet 1%-w Ru. Reduction of the metal to zero valent was achieved using sodium borohydride procedure exemplified as follows: 50 mL Sodium borohydride solution was added to the wet catalyst in a beaker. After 3 hours the reaction is finished, and resin is washed with excess HPLC water grade, filtered and dried at 90° C. overnight in vacuum oven under nitrogen sweep condition.

Example: AmberLyst™ 45 Ru Impregnated and Sodium Borohydride Reduction Step 12.0 g AmberLyst™ 45 charged into a reactor. 1.6 g $RuCl_3$, 0.4 g HCl and 256 g HPLC grade water was mix into an agitated vessel. Agitation at 200 rpm at room temperature done overnight. The content of the reactor were filtered and the metal impregnated resin isolated. A 100 mL water wash was done to this resin removing excess of Ru. The resin was then dried at 70° C. overnight in a vac oven with Nitrogen sweep. Yield was 14.1 g catalyst dry. 1%-w Ru. Reduction of the metal to zero valent was achieved using sodium borohydride procedure exemplified as follows: 50 mL Sodium borohydride solution was added to the dry catalyst in a beaker. After 3 hours the reaction was finished, and resin was washed with excess HPLC water grade, filtered and dried at 90° C. overnight in vacuum oven under nitrogen sweep condition.

Example: AmberLyst™ CH28 Pd Impregnated Commercially Available Sample 50 mL of AmberLyst™ CH28 were dried overnight at 90° C. overnight in vacuum oven under nitrogen sweep condition. 50 mL Sodium borohydride solution was added to the wet catalyst in a beaker. After 3 hours the reaction was finished, and resin was washed with excess HPLC water grade, filtered and dried at 90° C. overnight in vacuum oven under nitrogen sweep condition. At the end of the process the resin acid sites were neutralized to Na form and the Pd(II) reduced to Pd(0). Pd content is 0.7 mg-Pd per g of resin.

Example: AmberLyst™ 45 Ru Impregnated and Hydrogenation in Column Reduction Step 12.0 g AmberLyst™ 45 charged into a reactor. 1.6 g $RuCl_3$, 0.4 g HCl and 256 g HPLC grade water was mix into an agitated vessel. Agitation at 200 rpm at room temperature done overnight. The content of the reactor was filtered and the metal impregnated resin isolated. The resin was then dried at 70° C. overnight in a vacuum oven with Nitrogen sweep. Yield was 14.1 g catalyst dry. 1%-w Ru. Dry catalyst was charged into a column where hydrogen was passed in continuous process at 125 psi and 60° C. overnight. The reactor was then nitrogen-swept and catalyst unloaded from the reactor to be used later in time.

Example: AmberLyst™ 131 Ni Impregnated and Sodium Borohydride Reduction Step 50 mL AmberLyst™ 131 WET charged into a reactor. 17.5 g $NiSO_4$ heptahydrated salt, 2 g HCl and 256 g HPLC grade water was mix into an agitated vessel. Agitation at 200 rpm at room temperature done overnight. The contents of the reactor were filtered and the metal impregnated resin isolated. The resin was then dried at 70° C. overnight in a vac oven with Nitrogen sweep. Yield was 48 mL catalyst wet.

4.8%-w Ru. Reduction of the metal to zero valent was achieved using sodium borohydride procedure exemplified as follows: 50 mL Sodium borohydride solution was added to the dry catalyst in a beaker. After 3 hours the reaction was finished, and resin was washed with excess HPLC water grade, filtered and dried at 90° C. overnight in vacuum oven under nitrogen sweep condition. Nickel content in the final resin was 4.8%-w dry basis of resin.

TABLE 1

Properties for polymeric supports for the metals:

| | Commercial Catalysts for Metal Loading | ionic form | gellular or macro-reticular | water retention capacity (%) | volume exchange capacity (meq/mL) | average particle size (μm) | particle size distribution |
|---|---|---|---|---|---|---|---|
| I | | | | | | | |
| II | AmberLite ™ FPC16UPS Na | Na | Gellular | 42-48 | 2.0 | 600 | Uniform |
| II | AmberLite ™ CR 99Ca/310 | Ca | Gellular | 60-64 | 1.4 | 305 | Uniform |
| IV | AmberLite ™ FPC88 UPS Na | Na | Macro-reticular | 42-50 | 1.8 | 550 | Uniform |
| VI | AmberLite ™ FPC22 H | H | Macro-reticular | 52-58 | 1.7 | 600-800 | Normal |
| VIII | AmberLyst ™ BD10 DRY | H | Gellular | 44-51 | 4.9 eq/kg | 650 | Normal |
| XV | AmberLyst ™ 15 WET | H | Macro-reticular | 52-57 | 1.8 | 600-850 | Normal |
| XVII | AmberLyst ™ 46 | H | Macro-reticular | 26-36 | 1.3 eq/kg | 750 | Normal |
| XX | AmberLyst ™ 131 WET | H | Gellular | 62-68 | 1.35 meq/mL 4.8 eq/kg | 700-800 | Uniform |

TABLE 2

Catalyst Synthesis and Processing Conditions:

| Run Id. | Commercial Catalysts for Metal Loading | Ionic Form of Catalyst | Metal Loaded | Metal Reduction Method | %-Metal Dry Catalyst |
|---|---|---|---|---|---|
| I | Raney ™ Nickel 2400 | — | Ni | NaBH$_4$ | 80 |
| II | AmberLite ™ FPC16UPS Na | Na | Ru | H$_2$ | 5 |
| III | AmberLite ™ CR 99Ca/310 | Ca | Ru | H$_2$ | 5 |
| IV | AmberLite ™ FPC88 UPS Na | Na | Ru | H$_2$ | 5 |
| V | AmberLite ™ CR 99Ca/310 | Ca | Ru | H$_2$ | 1 |
| VI | AmberLite ™ FPC22 H | H | Ru | H$_2$ | 5 |
| VII | AmberLite ™ CR 99Ca/310 | Ca | Ru | H$_2$ | 5 |
| VIII | AmberLyst ™ BD10 | H | Ru | NaBH$_4$ | 5 |
| IX | AmberLyst ™ BD10-Repeat 2 | H | Ru | NaBH$_4$ | 5 |
| X | AmberLyst ™ BD10-Repeat 3 | H | Ru | NaBH$_4$ | 5 |
| XI | AmberLyst ™ BD10 | H | Ru | NaBH$_4$ | 5 |
| XII | AmberLyst ™ BD10-Repeat 2 | H | Ru | NaBH$_4$ | 5 |
| XIII | AmberLyst ™ BD10-Repeat 3 | H | Ru | NaBH$_4$ | 5 |
| XIV | AmberLyst ™ CH28 | H | Pd | H$_2$ | 0.7 |
| XV | AmberLyst ™ 15 WET | H | Ru | NaBH$_4$ | 1 |
| XVI | AmberLyst ™ 15 WET | H | Ru | NaBH$_4$ | 1 |
| XVII | AmberLyst ™ 46 | H | Ru | NaBH$_4$ | 0.5 |
| XIX | AmberLyst ™ 131 WET | H | Ru | NaBH$_4$ | 12 |
| XX | AmberLyst ™ 131 WET | H | Ni | H$_2$ | 5 |

TABLE 3

Sorbitol Synthesis: Process conditions and runs in the laboratory.

| | Catalyst | Glucose conc. (%) | Glucose g | Catalyst (g) | water (g) | temp. (° C.) | press. (psi) | process |
|---|---|---|---|---|---|---|---|---|
| I | Raney ™ Nickel 2400 | 11 | 2. | 5.0 | 225 | 150 | 400 | batch |
| II | AmberLite FPC16UPS Na | 11 | 25 | 5.0 | 225 | 120 | 400 | batch |
| III | AmberLite CR 99Ca /310 | 45 | 63 | 10.0 | 140 | 130 | 700 | batch |
| IV | AmberLite FPC88 UPS Na | 42 | 63 | 10.0 | 150 | 140 | 700 | batch |
| V | AmberLite CR 99Ca /310 | 42 | 63 | 10.0 | 150 | 140 | 700 | batch |

TABLE 3-continued

| | | Glucose conc. (%) | Glucose g | Catalyst (g) | water (g) | temp. (° C.) | press. (psi) | process |
|---|---|---|---|---|---|---|---|---|
| | Catalyst | | | | | | | |
| VI | AmberLite FPC22 H | 42 | 63 | 9.6 | 150 | 130 | 700 | batch |
| VII | AmberLite CR 99Ca/310 | 42 | 63 | 10.0 | 150 | 130 | 700 | batch |
| VIII | AmberLyst ™ BD10 | 26 | 63 | 7.0 | 240 | 120 | 800 | semi-cont. |
| IX | AmberLyst ™ BD10-Repeat 2 | 26 | 63 | 7.0 | 240 | 120 | 800 | semi-cont. |
| X | AmberLyst ™ BD10-Repeat 3 | 45 | 63 | 7.0 | 140 | 120 | 800 | semi-cont. |
| XI | AmberLyst ™ BD10 | 33 | 63 | 9.0 | 190 | 130 | 250 | semi-cont. |
| XII | AmberLyst ™ BD10-Repeat 2 | 33 | 63 | 9.0 | 190 | 130 | 250 | semi-cont. |
| XIII | AmberLyst ™ BD10-Repeat 3 | 45 | 63 | 9.0 | 140 | 130 | 700 | semi-cont. |
| XIV | AmberLyst ™ CH28 | 10 | 3 | 3.0 | 27 | 120 | 250 | batch |
| XVI | AmberLyst ™ 15 WET | 10 | 3 | 3.0 | 27 | 120 | 250 | batch |
| XVII | AmberLyst ™ 15 WET | 10 | 3 | 3.0 | 27 | 120 | 250 | batch |
| XVIII | AmberLyst ™ 46 | 10 | 3 | 3.0 | 27 | 120 | 250 | batch |
| XIV | AmberLyst ™ 131 WET | 10 | 3 | 3.0 | 27 | 120 | 250 | batch |
| XX | AmberLyst ™ 131 WET | 10 | 63 | 10 | 225 | 120 | 400 | patch |

Note:
Sugar hydrogenations were done in 24 h for run identification I to XIII and 2 h for IX to XVI.

TABLE 4

| | metal | catalyst (g) | glucose (g) | water (g) | temp. ( C) | reaction time (h) | Sorbitol Yield (%) |
|---|---|---|---|---|---|---|---|
| AmberLyst ™ CH28 | Pd | 3 | 3 | 27 | 120 | 15 | 2.9 |
| AmberLyst ™ 15 | Ru | 1 | 3 | 27 | 120 | 2 | 10.6 |
| AmberLyst ™ 15 | Ru | 1 | 3 | 27 | 120 | 2 | 9.5 |
| AmberLyst ™ 46 | Ru | 1 | 3 | 27 | 120 | 2 | 6.7 |
| AmberLyst ™ 131 | Ru | 1 | 3 | 27 | 120 | 2 | 71.2 |
| Raney Nickel | Ni | 6 | 3 | 27 | 140 | 7 | 100 |
| Ni 0104P | Ni | 3 | 3 | 27 | 120 | 7 | 100 |
| Raney Nickel | Ni | 2.3 | 9 | 27 | 120 | 2 | 100 |
| Ni/SiO$_2$ Al$_2$O$_3$ | Ni | 1 | 3 | 27 | 120 | 12 | 100 |
| Pd/Activated Carbon | Pd | 1.5 | 3 | 27 | 120 | 7 | 42.1 |

Sugar Hydrogenation Reactions

Glucose or Fructose or Sucrose hydrogenation reactions were carried out with a 10-50% aqueous glucose solution and specified amount of catalyst in a 450 mL Parr Reactor at a temperature of 120-160° C. and at 240-800 psig (1.66-5.52 MPa) H$_2$ pressure for 24 hours. Reactions were carried on using batch charged or particle charged into the reactor and semi-continuous addition of glucose/water for the first 3 hours of the process. All the Ru and Ni loaded ion-exchange resin catalysts tested had 1.0-14 g/L metal loading unless otherwise stated. After the desired reaction time, the reactor was cooled down to ambient temperature and the pressure was slowly released. The reactor content was filtered into a sample vial for subsequent work up and/or analysis using

$^1$HNMR, $^{13}$CNMR or HPLC. The quantitation of conversion of glucose and yield of sorbitol were determined based on the analytical method described below. The results of the catalyst activity tests have been delineated in Table 2. Hydrogenations were carried out as described above, except as otherwise noted in the tables. The data are presented in Tables 3, 4 and 5.

An existing metal-loaded AMBERLYST™ product, AMBERLYST™ CH28 resin, was also tested in glucose hydrogenation. The product is sold in an acid and unreduced form. The catalyst has been tested in acidic and neutralized forms with in situ reduction. These catalysts demonstrated extremely low activities in glucose hydrogenation as demonstrated by the very low conversions at long reaction times. AMBERLYST™ CH28 contains 2.8 g-Pd per liter resin.

Example: Sorbitol Synthesis: AmberLite™
FPC88UPS H Impregnated with 5% Ru. (Table 5)

In a 450 mL Parr Reactor were charged 10.0 g AmberLite FPC88UPS Na −5% Ru impregnated, 100 mL of deionized water, and 63 g glucose in 150 mL deionized water solution. The agitation speed fixed at 400 rpm, reaction temperature 140° C. and pressure of 700 psi H2. The reaction was ran for 24 h. At the end of this time the pressure was lowered to atmospheric pressure and temperature to room temperature. Liquid sample was taken and measured by HPLC method. The sample was stored at the freezer until it was analyzed by the HPLC method. At the end of the process the solution was analyzed by ICP to identify the Ru that was in solution and non detectable with <0.1 ppm limit by this method and equipment, demonstrating that at most a negligible amount of Ru had been leached from the catalyst during use.

TABLE 5

| | | glucose conversion (%) | sorbitol selectivity (%) | sorbitol yield (%) | measurement method |
|---|---|---|---|---|---|
| | Catalyst | | | | |
| I | Raney ™ Nickel 2400 | 98.09 | 56.33 | 55.26 | HPLC |
| II | AmberLite ™ FPC16UPS Na | 98.6 | 98.3 | 96.9 | HPLC |
| III | AmberLite ™ CR 99Ca/310 | 99.6 | 98.3 | 97.9 | HPLC |
| IV | AmberLite ™ FPC88 UPS Na | 99.8 | 97.9 | 97.9 | HPLC |
| V | AmberLite ™ CR 99Ca/310 | 99.8 | 99.0 | 99.1 | HPLC |
| VI | AmberLite ™ FPC22 H | 94.4 | 97.8 | 92.3 | HPLC |
| VII | AmberLite ™ 99Ca/310 | 95.1 | 76.1 | 72.4 | HPLC |
| VIII | AmberLyst ™ BD10 | 41.9 | 88.5 | 37.1 | HPLC |
| IX | AmberLyst ™ BD10-Repeat 2 | 39.1 | 95.7 | 37.4 | HPLC |
| X | AmberLyst ™ BD10-Repeat 3 | 38.6 | 97.2 | 37.5 | HPLC |
| XI | AmberLyst ™ BD10 | 62.5 | 89.1 | 55.7 | HPLC |
| XII | AmberLyst ™ BD10-Repeat 2 | 64.3 | 93.8 | 60.3 | HPLC |
| XIII | AmberLyst ™ BD10-Repeat 3 | 99.5 | 97.1 | 96.6 | HPLC |
| XIV | AmberLyst ™ CH28 | Nr | Nr | 2.9 | NMR |
| XV | AmberLyst ™ 15 WET | Nr | Nr | 10.6 | NMR |
| XVI | AmberLyst ™ 15 WET | Nr | Nr | 9.5 | NMR |
| XVII | AmberLyst ™ 46 | Nr | Nr | 6.7 | NMR |
| XIX | AmberLyst ™ 131 WET | nr | Nr | 71.2 | NMR |
| XX | AmberLyst ™ 131 WET | 1.8 | 95 | 0.05 | HPLC |

Example: Mannitol Synthesis: AmberLite™ FPC88UPS Na Impregnated with 5% Ru. (Table 6)

In a 450 mL Parr Reactor were charged 10.0 g AmberLite™ FPC88UPS Na –5% Ru impregnated, 100 mL of deionized water, and 63 g mannitol in 150 mL deionized water solution. The agitation speed fixed at 400 rpm, reaction temperature 140° C. and pressure of 700 psi $H_2$. The reaction was run for 24 h. At the end of this time the pressure was lowered to atmospheric pressure and temperature to room temperature. Liquid sample was taken and measured by HPLC method. The sample was stored at the freezer until it was analyzed by the HPLC method.

TABLE 6

| | | fructose conversion (%) | mannitol selectivity (%) | mannitol yield (%) | measurement method |
|---|---|---|---|---|---|
| | catalyst | | | | |
| IV | AmberLite ™ FPC88 UPS Na | 97.8 | 88.4 | 86.4 | HPLC |

The invention claimed is:

1. A method for reduction of sugars to sugar alcohols; said method comprising the steps of:
   a) providing a solution of a sugar comprising from five to twenty carbon atoms; and
   b) contacting said solution with hydrogen gas and a catalyst;
   wherein said catalyst comprises an ion exchange resin comprising Ru; and wherein the total loading of Ru on the ion exchange resin is from 0.5 to 200 g/liter of resin.

2. The method of claim 1 in which the ion exchange resin is a gel resin comprising from 1 to 10 wt % polymerized units of crosslinker or a macroreticular resin comprising from 8 to 20 wt % polymerized units of crosslinker.

3. The method of claim 2 in which said catalyst further comprises at least one of Mo, W, V, Mn, Re, Fe, Zr, Cu, Zn, Cr, Ge, Sn, Ti, Ni, and Au.

4. The method of claim 2 in which the sugar comprises from five to twelve carbon atoms.

5. The method of claim 2 in which the ion exchange resin is a styrenic resin which has acidic sites in an amount from 0.9 to 2.5 eq./liter of resin.

6. The method of claim 2 in which the ion exchange resin has a harmonic mean size from 200 to 1100 microns.

7. The method of claim 6 in which the sugar comprises from five to twelve carbon atoms.

8. The method of claim 7 in which the ion exchange resin is a styrenic resin which has acidic sites in an amount from 0.9 to 2.5 eq./liter of resin.

9. The method of claim 7 in which the sugar is glucose or fructose.

10. The method of claim 9 in which the ion exchange resin is a macroreticular resin comprising from 10 to 20 wt % polymerized units of crosslinker.

11. The method of claim 9 in which ion exchange resin is a gel resin comprising from 2 to 8 wt % polymerized units of crosslinker.

* * * * *